United States Patent
Wong et al.

(10) Patent No.: US 7,557,205 B2
(45) Date of Patent: Jul. 7, 2009

(54) 16-MEMBER RING METAL CHELATE

(75) Inventors: Kwok-Yin Wong, Hong Kong (CN); Chi Huang, Wuhan (CN); Cheuk-Sang Kwok, Toronto (CA); Victor Snieckus, 23 Earl Street, Kingston, Ontario (CA) K7L 2G4

(73) Assignees: The Hong Kong Polytechnic University, Hong Kong Sar (CN); Victor Snieckus, Kingston (CA)

( * ) Notice: Subject to any disclaimer, the term of this patent is extended or adjusted under 35 U.S.C. 154(b) by 612 days.

(21) Appl. No.: 10/948,458

(22) Filed: Sep. 24, 2004

(65) Prior Publication Data

US 2006/0069249 A1    Mar. 30, 2006

(51) Int. Cl.
*C07B 47/00*    (2006.01)

(52) U.S. Cl. ..................................................... 540/145

(58) Field of Classification Search .................. 540/145
See application file for complete search history.

(56) References Cited

U.S. PATENT DOCUMENTS 6,881,732 B2 *   4/2005   Winchell ..................... 514/183

* cited by examiner

*Primary Examiner*—James O. Wilson
*Assistant Examiner*—Paul V. Ward
(74) *Attorney, Agent, or Firm*—Buchanan Ingersoll & Rooney PC

(57) ABSTRACT

Metal chelates are useful for improving the contrast of X-ray, ultrasound, radionuclide and magnetic resonance (MR) images. However, the metal complexes must be stable and inert so that toxicity resulting from dissociation in the body can be minimized. This invention provides 16-member ring metal chelates that can provide a charge balanced metal complex having improved stability, especially for gadolinium(III) and samarium (III).

5 Claims, 3 Drawing Sheets

Figure 2a
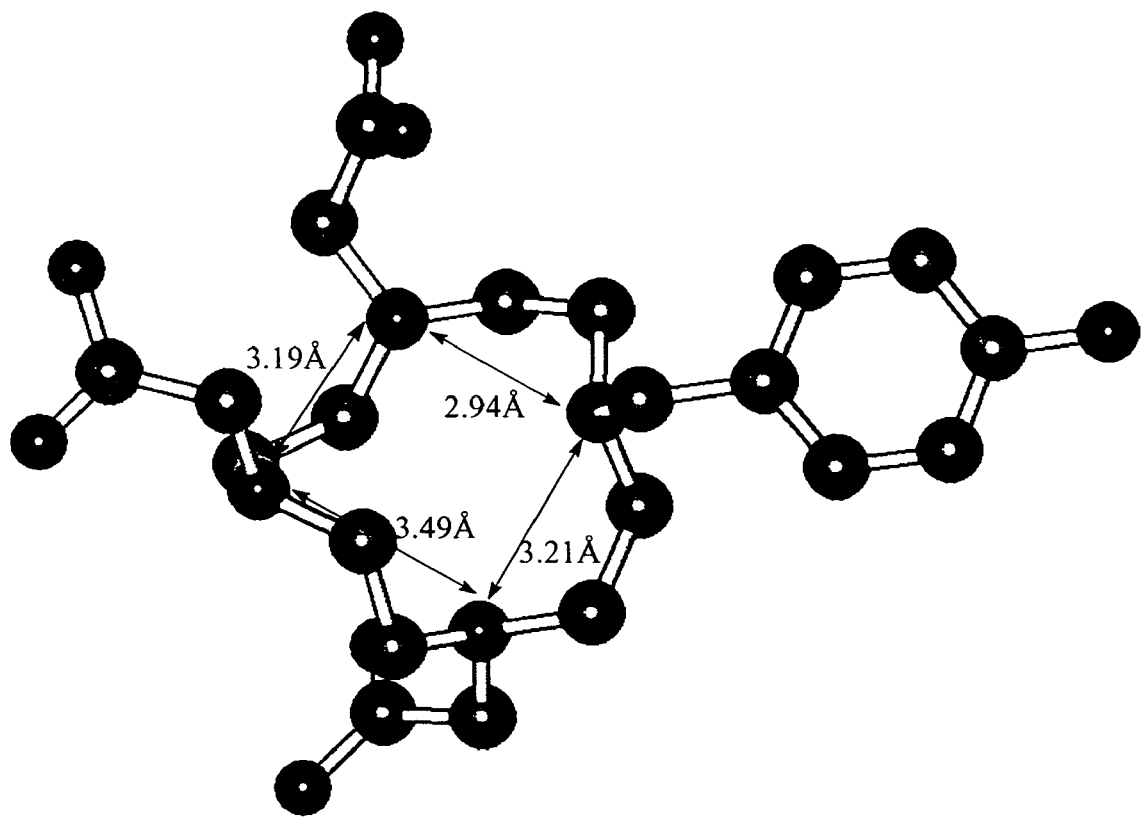
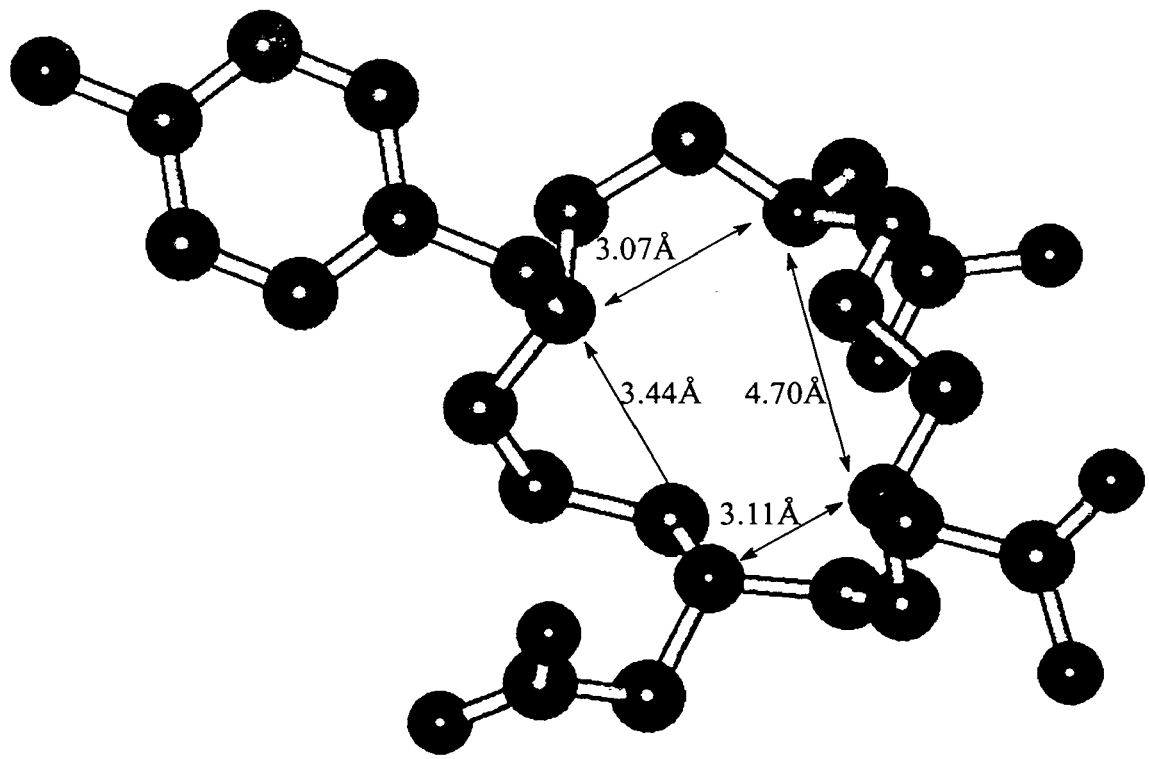
Figure 2b

16-MEMBER RING METAL CHELATE

FIELD OF THE INVENTION

This invention relates to macrocyclic chelate ligands for metal ions, particularly those for gadolinium and samarium.

BACKGROUND OF THE INVENTION

Metal chelates are useful for improving the contrast of X-ray, ultrasound, radionuclide and magnetic resonance (MR) images. However, the metal complexes must be stable and inert so that toxicity resulting from dissociation in the body can be minimized. Further, highly stable chelates of paramagnetic ions, like gadolinium(III), are used to reduce the longitudinal and transverse relaxation times T1 and T2 of water in MRI. Samarium (III), particularly $^{153}$Sm can emit both gamma radiation for imaging and beta radiation for localized radiation.

A variety of chelates, including derivatives of DTPA (diethylenetriaminepentaacetic acid) or DOTA (1,4,7,10-tetraazacyclododecane-1,4,7,10-tetraacetic acid) were used to chelate $Gd^{3+}$ ions. However, such chelates are not charge balanced and such may lower the stability of the resulting metal complex.

OBJECTS OF THE INVENTION

Therefore, it is an object of this invention to provide an improved chelate for paramagnetic ions to resolve at least one or more of the problems as set forth in the prior art. As a minimum, it is an object of this invention to provide the public with a useful choice.

SUMMARY OF THE INVENTION

Accordingly, this invention provides a metal chelate having the Formula I:

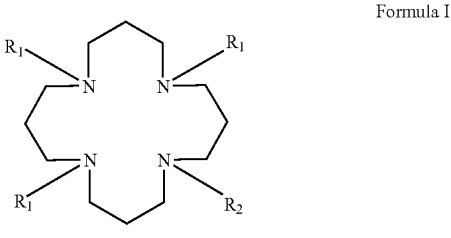

Formula I wherein
  $R_1$ is an anionic group having minus one charge; and
  $R_2$ is a chemically reactive group capable of forming a linkage with a biomolecule.
  Preferably, $R_1$ is selected from the group consisting of $-CH_2COO^-$ and $-CH_2SO_3^-$ groups. More preferably, $R_1$ is $-CH_2COO^-$.
  Optionally, the chemically reactive group $R_2$ is selected from the group consisting of $-(CH_2)_n-R_5$, $-(CH_2)_n-C_6H_4-R_5$, wherein $R_5$ capable of reacting and forming a linkage with a biomolecule and n is an integer equal to or greater than 1. More preferably, $R_5$ is selected from the group consisting of $NO_2$, $NH_2$, NCS, $N_2^+$, and $NHCOCH_2Br$.

It is another aspect of this invention to provide a method of synthesizing A metal chelate having the Formula I.

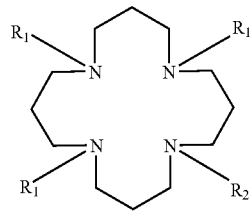

Formula I

First, compounds of Formula II and Formula III are reacted to form a compound of Formula IV.

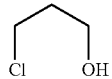

Formula II

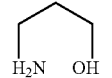

Formula III

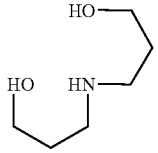

Formula IV

Then a molecule having chemically reactive group $R_2$ reacts with the compound of Formula IV to replace the hydrogen on the N—H group of Formula IV. The hydrogen on the two O—H groups of Formula IV is replaced with a first leaving group $L_1$ to form a compound of Formula V

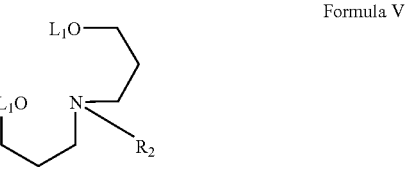

Formula V

Moreover, one hydrogen of each nitrogen of a compound of Formula VI is replaced with a second leaving group $L_2$, and then with a metal alkoxide to replace the terminal hydrogen with the metal to form a compound of Formula VII.

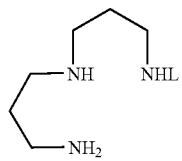

Formula VI

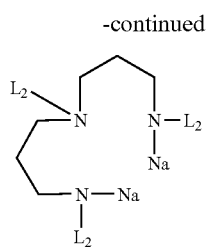

Formula VII

Finally, the compounds of Formula V and Formula VII react, and then the second leaving groups $L_2$ are replaced with a $R_1$ group to form the compound of Formula I.

BRIEF DESCRIPTION OF THE DRAWINGS

Preferred embodiments of the present invention will now be explained by way of example and with reference to the accompanying drawings in which:

FIG. 2 shows the molecular models of the N-p-aminobenzyl derivative of DOTA (12-membered chelate) (2a) and TETA (14-membered chelate) (2b) of the prior art.

DETAILED DESCRIPTION OF THE PREFERRED EMBODIMENT

Figure 1:
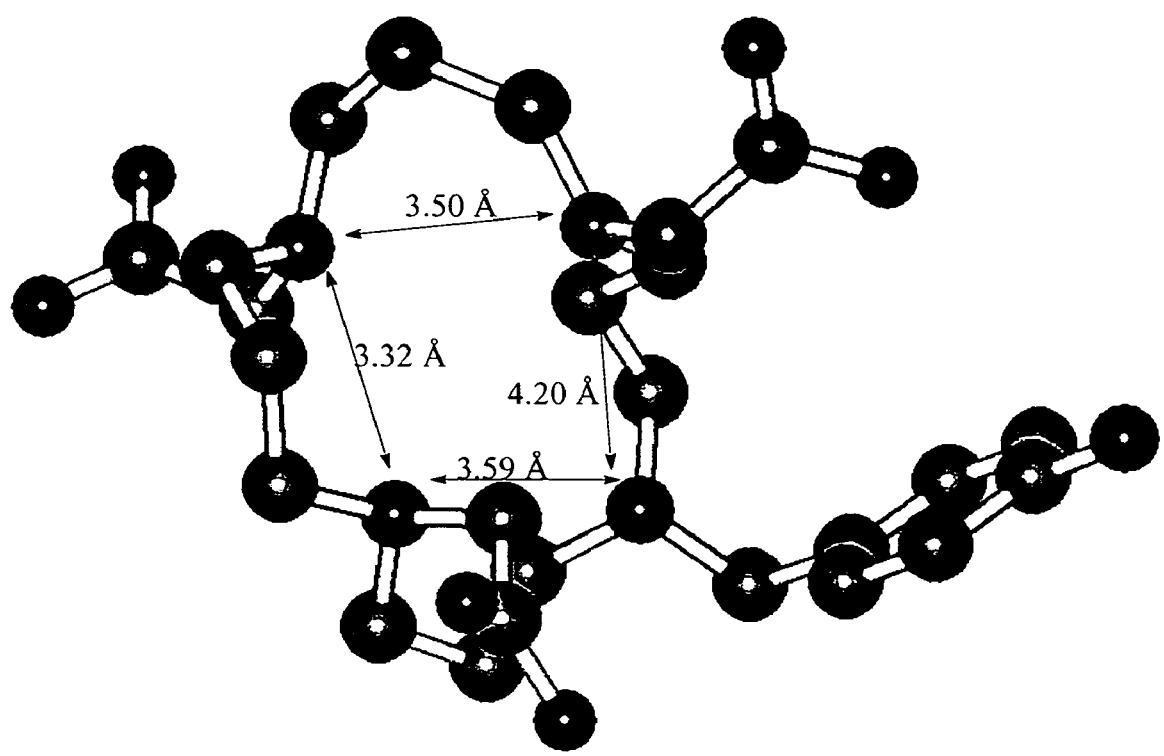
FIG. 1 shows the molecular model of an exemplary 16-member ring chelate, N-p-aminobenzyl-1,5,9,13-tetraazacyclohexadecane-N',N'',N'''-triacetic acid (HETA), of this invention, indicating the size of the chelate cavity.

This invention is now described by way of example with reference to the figures in the following paragraphs. List 1 is a part list so that the reference numerals in the figures may be easily referred to.

To accommodate the relatively large $Gd^{3+}$ or $Sm^{3+}$ ions, a 16-membered ring chelate is synthesized. The chemical structure of this chelate is shown in Formulae I below:

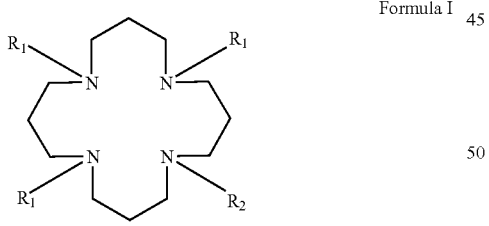

Formula I $R_1$ is anionic group like $—CH_2COO^-$ or $—CH_2SO_3^-$ groups, and $R_2$ is a chemically reactive group capable of forming a linkage with a biomolecule. The three $R_1$ groups provides additional three ligands for the $Gd^{3+}$ or $Sm^{3+}$ ions, and charge balance to the whole resulting complex. This may not only increase the stability, but may also decrease the osmolality and viscosity of the complex in solution because the negative charge on the anionic $R_1$ group would enhance the solubility of the metal complex in water.

The chemically reactive group can be anyone of $—(CH_2)_n—R_5$, $—(CH_2)_n—C_6H_4—R_5$ (n is an integer equal to or greater than 1. The basic requirement is that the group shall contain a functional group $R_5$ capable of reacting and forming a linkage with a biomolecule. For example, $R_5$ can be $NO_2$, $NH_2$, NCS, $N_2^+$, $NHCOCH_2Br$.

The molecular model of an example of 16-membered ring chelate is shown in FIG. 1, wherein the chemically reactive group is aminobenzyl. The molecular model of DOTA and TETA of the prior art are shown in FIG. 2a and FIG. 2b respectively for comparison. It can be seen that the 16-member chelate has a larger central cavity than the 12-membered DOTA and 14-membered TETA to accommodate metal ions of large size. FIG. 1 also shows the distances between the N-ligands in the ring of HETA.

The 16-membered ring chelate of this invention may be synthesized by the following steps:

reacting compounds of Formula II and Formula III to form a compound of Formula IV Formula II Formula III Formula IV reacting a molecule having chemically reactive group to replace the hydrogen on the N—H group of Formula IV. The molecule having chemically reactive group would have good leaving group to react with the hydrogen on the N—H group. For example, if the chemically reactive group is p-nitrobenzyl, p-nitrobenzyl bromide may be used. Of course, molecule other than those having bromide may be used, particularly if other chemically reactive groups are desired. Finding a suitable candidate shall be a trial-and-error exercise to a person skilled in the art.

replacing the hydrogen on the two O—H groups of Formula IV with a first leaving group $L_1$ to form a compound of Formula V

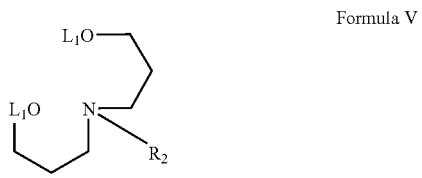

Formula V

Suitable first leaving group $L_1$ may include 2-mesitylenesulfonyl, or p-toluenesulfonyl. The method of replacement can be done be various methods known in the art.

replacing one hydrogen of each nitrogen of a compound of Formula VI with a second leaving group $L_2$, and then with a metal alkoxide to replace the terminal hydrogen with the metal to form a compound of Formula VII

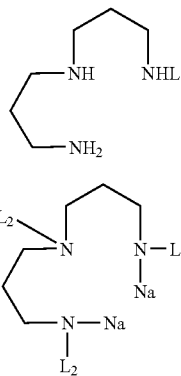

Formula VI

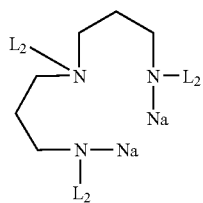

Formula VII

Suitable first leaving group $L_2$ may include 2-mesitylenesulfonyl, or p-toluenesulfonyl. Again, methods of replacing the hydrogen on N—H group are known in the art.

reacting the compounds of Formula V and Formula VII, and then replacing the second leaving group $L_2$ with a carboxylic acid group to form the compound of Formula I.

The synethesis of an exemplary chelate of this invention, 1-(p-nitrobenzyl)-5,9,13-tricarbobenzyloxymethyl-1,5,9, 13-tetraazacyclo-hexadecane, will be detailed in the following section.

EXAMPLE

Figure 3:
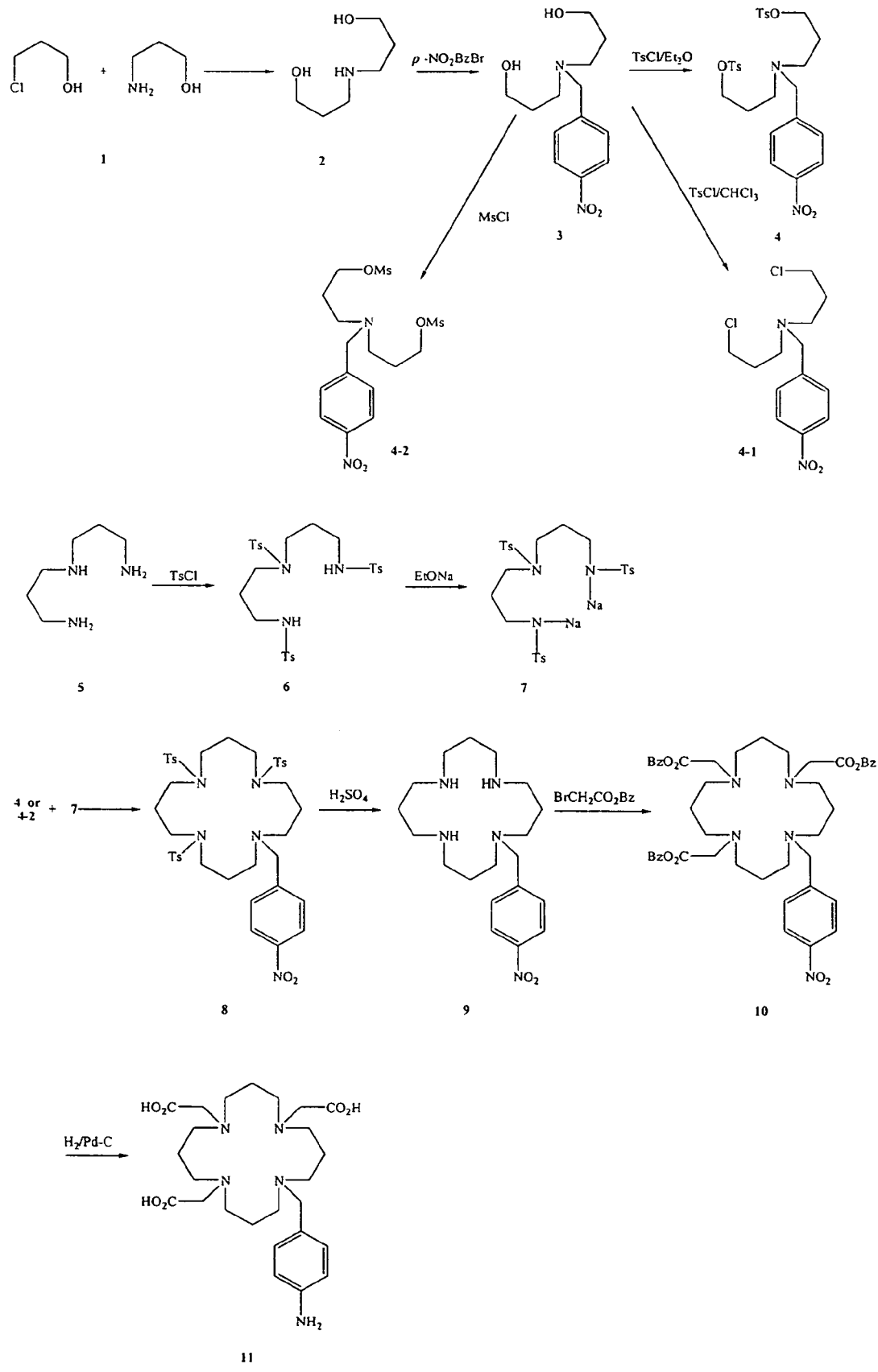
FIG. 3 shows an exemplary scheme of the synthesis of HETA.

FIG. 3 shows the synthetic route of an embodiment of the 16-membered ring chelate as shown in FIG. 1. The detailed steps will be described below.

Dipropanolamine (2)

A mixture of 3-amino-1-propanol (45 mL, 0.59 mol), 1-chloro-3-hydroxypropane (25 mL, 0.30 mol) and water (130 mL) was refluxed over 24 hours. Potassium hydroxide was then added. After dissolution, the whole of the water was evaporated to leave viscous oil and large quantities of potassium chloride. These were filtered and washed with dried acetone. The organic phase was dried over magnesium sulfate, filtered and evaporated to leave dark brown oil. The desired dipropanolamine was obtained, by distillation of this oil, as a colorless or light yellow liquid (m=31.5 g; 0.24 mol, yield=80%). 1H NMR $\delta$ (CDCl$_3$): 1.73 (q, 4H, N—CH$_2$—CH$_2$—CH$_2$—OH); 2.81 (t, 4H, N—CH$_2$—CH$_2$—CH$_2$—OH); 3.20 (s, 3H, HN—CH$_2$—CH$_2$—CH$_2$—OH), 3.75 (t, 4H, N—CH$_2$—CH$_2$—CH$_2$—OH).

N-(p-Nitrobenzyl)-dipropanolamine (3)

Dipropanolamine 2 (10.6 g, 80 mmol) and p-nitrobenzyl bromide (17.38 g, 80 mmol) in dried acetonitrile (110 mL) with dried potassium carbonate (22.0 g, 160 mmol) were reacted at 55~60 ☐ (the temperature of oil bath) for 2 h. The solid was filtered off and the solvent was evaporated. The yellow oil obtained was the desired compound 3 with purity above 99% by TLC. (m=21.5 g, quantitative yield). $^1$H NMR $\delta$ (CDCl$_3$): 1.78 (q, 4H, N—CH$_2$—CH$_2$—CH$_2$—OH); 2.64 (t, 4H, N—CH$_2$—CH$_2$—CH$_2$—OH); 3.61 (s, 2H, —OH); 3.68 (s, 2H, N—CH$_2$—C$_6$H$_4$—); 3.70 (t, 4H, N—CH$_2$—CH$_2$—CH$_2$—OH); 7.49 (d, 2H, C$_6$H$_4$(Bz)); 8.20 (d, 2H, C$_6$H$_4$(Bz)). $^{13}$C NMR $\delta$ (CDCl$_3$): 28.59(2C, N—CH$_2$—CH$_2$—CH$_2$—Cl); 52.68(2C, N—CH$_2$—CH$_2$—CH$_2$—OH); 58.31(1C, —N—CH$_2$-Bz); 62.23(2C, N—CH$_2$—CH$_2$—CH$_2$—Cl); 123.63(2C, C$_6$H$_4$(Bz)); 129.63(2C, C$_6$H$_4$(Bz)); 146.15(1C, C$_6$H$_4$(Bz)); 147.16(1C, C$_6$H$_4$(Bz)). TOF MS ESI: 269.21 ([M+H]$^+$).

1,9-Ditosyl-5-(p-nitrobenzyl)-1,9-dioxo-5-azanonane (4)

N-(p-Nitrobenzyl)-dipropropanolamine (3) (1.0 g, 3.7 mmol) and p-toluenesulfonyl chloride (1.9 g, 10 mmol) were dissolved in diethyl ether (50 mL). Triethylamine (10 mL) was added dropwise for 3 h under efficient stirring. The mixture was stirred for an additional 72 hours and allowed to stand overnight. The solid was dissolved in dichloromethane (50 mL) and washed with water (50 mL×3). The organic layer was dried over sodium sulfate and the solvent was evaporated to afford brown yellow oil. The oil was then subjected to silica gel chromatography using dichloromethane, which gave light yellow oil 4 (0.75 g, 35.4% yield). 1H NMR $\delta$ (CDCl$_3$): 1.75 (q, 4H, N—CH$_2$—CH$_2$—CH$_2$—NH); 2.44 (s, 6H, C$_6$H$_4$—CH$_3$); 2.44 (t, 4H, O—CH$_2$—CH$_2$—CH$_2$—N); 3.54 (s, 2H, N—CH$_2$—C$_6$H$_4$—); 4.04 (t, 4H, N—CH$_2$—CH$_2$—CH$_2$—O); 7.35 (t), 7.74 (t), 8.06 (d) (12H, C$_6$H$_4$).

N-(p-Nitrobenzyl)-di-(3-chloropropyl)amine(4-1)

N-(p-Nitrobenzyl)-dipropropanolamine (3) (21.0 g, 78 mmol) and p-toluenesulfonylchloride (30.0 g, 157 mmol) were dissolved in chloroform (100 mL). Triethylamine (30 mL) was added dropwise for 3 h under efficient stirring at refluxing. The mixture was stirred for an additional 12 hours at this temperature. The solution was washed with water (50 mL×3). The organic layer was dried over sodium sulfate and the solvent was evaporated to afford yellow oil. The resulting oil was then subjected to silica gel chromatography using dichlorometnane, which gave light yellow solid 4-1 (18.0 g, 74.0% yield, mp=☐). $^1$H NMR $\delta$ (CDCl$_3$): 1.93 (q, 4H, N—CH$_2$—CH$_2$—CH$_2$—Cl); 2.60 (t, 4H, N—CH$_2$—CH$_2$—CH$_2$—Cl); 3.59 (t, 4H, N—CH$_2$—CH$_2$—CH$_2$—Cl); 3.65 (s, 2H, —N—CH$_2$-Bz); 7.49 (d, 2H, C$_6$H$_4$(Bz)); 8.18 (d, 2H, C$_6$H$_4$(Bz)). $^{13}$C NMR $\delta$ (CDCl$_3$): 30.11(2C, N—CH$_2$—CH$_2$—CH$_2$—Cl); 42.77 (2C, N—CH$_2$—CH$_2$—CH$_2$—Cl); 50.88(2C, N—CH$_2$—CH$_2$—CH$_2$—Cl); 58.42(1C, —N—CH$_2$-Bz); 123.57(2C, C$_6$H$_4$(Bz)); 129.10(2C, C$_6$H$_4$(Bz)); 147.11(1C, C$_6$H$_4$(Bz)); 147.40(1C, C$_6$H$_4$(Bz)). TOFMS ESI: 305.05 ([M+H]$^+$).

1,9-Dimesityl-5-(p-nitrobenzyl)-1,9-dioxo-5-azanonane (4-2)

N-(p-Nitrobenzyl)-dipropropanolamine (3) (2.36 g, 8.8 mmol) and triethylamine (20 mL) were dissolved in dichloromethane (40 mL). 2-Mesitylenesulfonyl chloride (2.05 g, 17.6 mmol) in dichloromethane (30 mL) was added dropwise for 1.5 h under efficient stirring at refluxing. The mixture was stirred for an additional 1 hour at this temperature. The solution was washed with water (10 mL×3). The organic layer was dried over sodium sulfate and the solvent was evaporated to afford yellow oil. The resulting oil was then subjected to silica gel chromatography using dichloromethane:acetone=20:1, which gave 4-2 as a light brown oil (1.8 g, 48.2% yield). $^1$H NMR $\delta$ (CDCl$_3$): 1.94 (q, 4H, N—CH$_2$—CH$_2$—CH$_2$—OMs); 2.59 (t, 4H, N—CH$_2$—CH$_2$—CH$_2$—OMs); 3.00 (s, 6H, CH$_3$—SO$_2$—); 3.67 (s, 2H, —N—CH$_2$-Bn); 4.28 (t, 4H, N—CH$_2$—CH$_2$—CH$_2$—OMs); 7.49 (d, 2H, C$_6$H$_4$); 8.18 (d, 2H, C$_6$H$_4$). $^{13}$C NMR $\delta$ (CDCl$_3$): 26.83 (2C, N—CH$_2$—CH$_2$—CH$_2$—OMs); 37.26 (2C, N—CH$_2$—CH$_2$—CH$_2$—OMs); 49.83 (2C, N—CH$_2$—CH$_2$—CH$_2$—OMs); 61.46 (1C, —N—CH$_2$-Bn); 67.82 (2C, CH$_3$—SO$_2$—); 123.60 (2C, $C_6H_4$); 129.10 (2C, $C_6H_4$); 147.04 (1C, $C_6H_4$); 147.12 (1C, $C_6H_4$). TOF MS ESI: 425.09 ([M+H]$^+$).

1,5,9-Tritosyl-1,5,9-triazanonane (6)

1,5,9-triazanonane 5 (13.1 g, 0.1 mol) and sodium hydroxide (12.0 g, 0.3 mol) were dissolved in water (100 mL). A solution of p-toluenesulfonylchloride (57.2 g, 0.3 mol) in diethyl ether (200 mL) was added dropwise for 3 h under efficient stirring. The mixture was stirred for an additional 4 hours and allowed to stand overnight. Water and diethyl ether were decant and the oil was dissolved in dichloromethane. The solution was dried over sodium sulfate, filtered and evaporated to leave a thick glassy orange oil. Recrystallization in methanol afforted white crystalline solid (6) (m=57.2 g, yield=96.5%, mp=☐). $^1$H NMR δ (CDCl$_3$): 1.71 (q, 4H, N—CH$_2$—CH$_2$—CH$_2$—NH); 2.41 (s, 6H, $C_6H_4$—CH$_3$); 2.42 (s, 3H, $C_6H_4$—CH$_3$); 2.93 (t, 4H, N—CH$_2$—CH$_2$—CH$_2$—NH); 3.09 (t, 4H, N—CH$_2$—CH$_2$—CH$_2$—NH); 7.28, 7.62, 7.72 (12H, $C_6H_4$). TOF MS ESI: 594.1761 ([M+H]$^+$), 616.1556 ([M+Na]$^+$).

1,5,9-tritosyl-1,5,9-triazanonane disodium salt (7)

1,5,9-Tritosyl-1,5,9-triazanonane (6) (3.0 g, 5.0 mmol) was added to absolute ethanol (18 mL). The stirred slurry was heated to reflux. Sodium ethoxide solution (0.34 g sodium metal in 20 mL absolute ethanol) was slowly added to the solution for 1 h and the solution was refluxed for further 3 h. The white solid was precipitated. The solvent was evaporated and the white solid (7) obtained was used directly for the next cyclization step.

1,5,9-Tritosyl-13-(p-nitrobenzyl)-1,5,9,13-tetraazacyclo-hexadecane (8)

1,5,9-Tritosyl-1,5,9-triazanonane disodium salt (7) was dissolved in dry DMF (30 mL) and heated up to 110 ☐ under stirring. 1,9-Ditosyl-5-(p-nitrobenzyl)-1,9-dioxo-5-azanonane (4) (2.9 g, 5 mmol) was dissolved in 20 mL dry DMF and added dropwise to the solution for 3 h under nitrogen atmosphere at 110 ☐. The solution was kept at 110 ☐ for further 3 h and then was poured into water (800 mL). The brown yellow solid was precipitated. The solution was placed for 4 days. The solid was collected by filtration. The resulting solid was then subjected to silica gel chromatography using dichloromethane, followed by dichloromethane-acetone (40:1), which gave 8 (1.0 g, 24% yield, mp=1167.0-170.5 ☐). $^1$H NMR δ (CDCl$_3$): 1.76 (t, 4H, Ts-N—CH$_2$—CH$_2$—CH$_2$—N-Bz); 2.01 (t, 4H, Ts-N—CH$_2$—CH$_2$—CH$_2$—N-Ts); 2.43 (s, 6H, CH$_3$(Ts)); 2.45 (s, 3H, CH$_3$(Ts)); 2.50 (t, 4H, Ts-N—CH$_2$—CH$_2$—CH$_2$—N-Bz); 2.98 (t, 4H, Ts-N—CH$_2$—CH$_2$—CH$_2$—N-Bz), 3.13 (q, 8H, Ts-N—CH$_2$—CH$_2$—CH$_2$—N-Ts); 7.29 (d), 7.35 (d), 7.43 (d), 7.60 (d), 7.71 (d), 8.14 (d) (16H, $C_6H_4$). TOF MS ESI: 826.62([M+H]$^+$), 848.61 ([M+Na]$^+$)

It was found that the yield of using 4-1 in synthesizing 8 was quite low (less than 10%). However, it was also found that using 4-2 instead of 4 gives a yield of about 30%, which is comparable to using 4.

1-(p-nitrobenzyl)-1,5,9,13-tetraazacyclohexadecane (9)

1,5,9-Tritosyl-13-(p-nitrobenzyl)-1,5,9,13-tetraazacyclo-hexadecane (8) (1.5 g) was dissolved completely in concentrated sulfuric acid (3 mL) at 60 ☐. The clear solution was stirred and heated to 90 ☐ for 28 h. The resulting dark brown solution was cooled below 80 ☐ and then cooled in ice. Water (10 mL) was slowly added under very vigorous stirring. The solution was brought to pH>12 with sodium hydroxide and then extracted five times with dichloromethane (20, 40, 40, 10, 20 mL). The dichloromethane extract was dried with anhydrous sodium sulfate to give a yellow oil (9) (0.50 g, 76.7% yield). $^1$H NMR (CDCl$_3$): 1.68 (q, 4H, —HN—CH$_2$—CH$_2$—CH$_2$—NH); 1.77 (q, 4H, —HN—CH$_2$—CH$_2$—CH$_2$—NBn-); 2.51 (t, 4H, —HN—CH$_2$—CH$_2$—CH$_2$—NH—); 2.70 (t, 4H, —HN—CH$_2$—CH$_2$—CH$_2$—NH—); 2.78 (t, 4H, —HN—CH$_2$—CH$_2$—CH$_2$—NBn-); 2.82 (t, 4H, —CH$_2$—NBn-CH$_2$—); 3.62 (b, 3H, —HN—); 3.68 (s, 2H, —N—CH$_2$—$C_6H_4$—); 7.49 (d, 2H, NO$_2$—$C_6H_4$—); 8.18 (d, 2H, NO$_2$—$C_6H_4$—). TOF MS:

1-(p-nitrobenzyl)-5,9,13-tricarbobenzyloxymethyl-1,5,9,13-tetraazacyclo-hexadecane (10)

A solution of 9 (0.53 g, 1.4 mmol), benzyl bromoacetate, Cs$_2$CO$_3$ (4.56 g, 14.0 mmol) and Bu$_4$NBr (96.7 mg, 0.30 mmol) in THF:H$_2$O (50 mL: 5 mL) was refluxed for 12 h. THF was evaporated and the residue was extracted by CH$_2$Cl$_2$ (40 mL, 40 mL, 30 mL, 20 mL, 20 mL). The extract was dried with anhydrous sodium sulfate to yield a yellow oil. The resulting yellow oil was then subjected to silica gel chromatography using dichloromethane, followed by dichloromethane-methanol (40~30:1), which gave 10 (1.00 g, yield 84.9%). $^1$H NMR δ (CDCl$_3$): 1.58 (m, 8H, —N—CH$_2$—CH$_2$—CH$_2$—N—); 2.42 (t, 4H, —N—CH$_2$—CH$_2$—CH$_2$—N-Bz-NO$_2$); 2.5~2.7 (m, 12H, —OOCCH$_2$—N—CH$_2$—); 3.32 (s, 4H, —OOCCH$_2$—N—); 3.35 (s, 2H, —OOCCH$_2$—N—); 3.57 (s, 2H, -Bn-CH$_2$—N—); 5.10 (s, 4H, Bn-CH$_2$—COO—CH$_2$—N—); 5.13 (s, 2H, Bn-CH$_2$—COO—CH$_2$—N—); 7.2-7.4 (m, 15H, $C_6H_5$—CH$_2$—COO—CH$_2$—); 7.45 (d, 2H, NO$_2$—$C_6H_4$—); 8.14 (d, 2H, NO$_2$—$C_6H_4$—) (d), 7.35 (d), 7.43 (d), 7.60 (d), 7.71 (d), 8.14 (d) (15H, $C_6H_5$). $^{13}$C NMR, δ(CDCl$_3$): 25.16(2C, —OOCCH$_2$N—CH$_2$—CH$_2$—CH$_2$—NCH$_2$COO—); 25.68(2C, —OOCCH$_2$N—CH$_2$—CH$_2$—CH$_2$—N-Bz-NO$_2$); 51.59(4C, —OOCCH$_2$N—CH$_2$—CH$_2$—CH$_2$—NCH$_2$COO—); 51.63(2C, —OOCCH$_2$N—CH$_2$—CH$_2$—CH$_2$—N-Bz-NO$_2$); 51.93(2C, —OOCCH$_2$N—CH$_2$—CH$_2$—CH$_2$—N-Bz-NO$_2$); 55.46(2C, —N—CH$_2$—COO—); 55.59(1C, N—CH$_2$—COO—); 58.80(1C, —N—CH$_2$—$C_6H_4$—NO$_2$); 65.82(3C, —COO—CH$_2$—$C_6H_5$); 123.41(3C, —CH$_2$—$C_6H_4$—NO$_2$); 128.05(4C, $C_6H_5$—CH$_2$); 128.08(4C, $C_6H_5$—CH$_2$); 128.10(2C, $C_6H_5$—CH$_2$); 128.33(4C, $C_6H_5$—CH$_2$); 128.35(2C, $C_6H_5$—CH$_2$); 128.93(2C, $C_6H_5$—CH$_2$); 135.62 (3C, —CH$_2$—$C_6H_4$—NO$_2$); 171.12(2C, —CH$_2$—COO—); 171.16(1C, —CH$_2$—COO—). HRMS (ESI): m/z Calcd. for $C_{46}H_{58}N_5O_6$ ([M+H]$^+$): 808.4285; Found: 808.4249.

1-(p-aminobenzyl)-5,9,13-tricarboxymethyl-1,5,9,13-tetraazacyclohexadecane (11)

A mixture of 10 (0.13 g, mmol), NaOH (0.15 g), water (1 mL), MeOH (4 mL) and 10% Pd—C in 50% water (31.2 mg) was hydrogenated at 4 atm at room temperature for 24 h. $^1$H NMR δ (D$_2$O): 1.34 (m, 8H, —N—CH$_2$—CH$_2$—CH$_2$—N—); 2.24 (t, 4H, —N—CH$_2$—CH$_2$—CH$_2$—N-Bn-NO$_2$); 2.30 (m, 12H, HOOCCH$_2$—N—CH$_2$—); 2.90 (s, 4H, —OOCCH$_2$—N—); 2.91 (s, 2H, —OOCCH$_2$—N—); 3.29 (s, 2H, -BzCH$_2$—N—); 6.60 (d, 2H, —$C_6H_4$—NH$_2$); 6.93 (d, 2H, —$C_6H_4$—NH$_2$). HRMS (ESI): m/z cacl. for $C_{25}H_{42}N_5O_6$ ([M+H]$^+$): 508.3134; found: 508.3148.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

The invention claimed is:

1. A metal chelate having the Formula I:

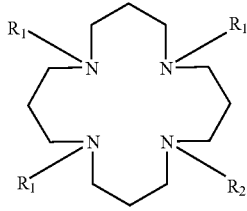

Formula I wherein
R$_1$ is an anionic group having minus one charge selected from the group consisting of —CH$_2$COO$^-$ and —CH$_2$SO$_3^-$ groups; and
R$_2$ is a chemically reactive group selected from the group consisting of —(CH$_2$)$_n$—R$_5$, —(CH$_2$)$_n$—C$_6$H$_4$—R$_5$, wherein R$_5$ is capable of reacting and forming a linkage with a biomolecule and n is an integer equal to or greater than 1, wherein R$_5$ is selected from the group consisting of NO$_2$, NH$_2$, NCS, N$_2^+$, and NHCOCH$_2$Br.

2. The metal chelate of claim 1, wherein R$_1$ is —CH$_2$COO$^-$.

3. A method of synthesizing the metal chelate of claim 1, comprising the steps of:

reacting compounds of Formula II and Formula III to form a compound of Formula IV

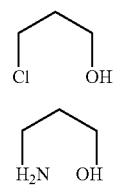

Formula II

Formula III

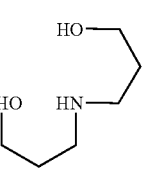

Formula IV reacting a molecule having chemically reactive group R$_2$ with the compound of Formula IV to replace the hydrogen on the N—H group of Formula IV;
replacing the hydrogen on the two O—H groups of Formula IV with a first leaving group L$_1$ to form a compound of Formula V

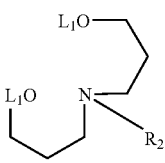

Formula V replacing one hydrogen of each nitrogen of a compound of Formula VI with a second leaving group L$_2$, and then with a metal alkoxide to replace the terminal hydrogen with the metal to form a compound of Formula VII

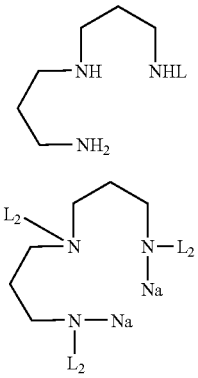

Formula VI

Formula VII reacting the compounds of Formula V and Formula VII, and then replacing the second leaving groups L$_2$ with R$_1$ groups to form the compound of Formula I, wherein R$_1$ is selected from the group consisting of —CH$_2$COO$^-$ and —CH$_2$SO$_3^-$ groups.

4. The method of claim 3, wherein R$_1$ is —CH$_2$COO$^-$.

5. The method of claim 3, wherein the chemically reactive group R$_2$ is selected from the group consisting of —(CH$_2$)$_n$—R$_5$, —(CH$_2$)$_n$—C$_6$H$_4$—R$_5$, wherein R$_5$ is capable of reacting and forming a linkage with a biomolecule and n is an integer equal to or greater than 1, wherein R$_5$ is selected from the group consisting of NO$_2$, NH$_2$, NCS, N$_2^+$, and NHCOCH$_2$Br.

* * * * *